US00PP26282P2

(12) United States Plant Patent

Fell, Jr.

(10) Patent No.: US PP26,282 P2

(45) Date of Patent: Dec. 29, 2015

(54) *PHILODENDRON* PLANT NAMED 'LITTLE HOPE'

(50) Latin Name: *Philodendron selloum*
Varietal Denomination: Little Hope

(71) Applicant: David N. Fell, Jr., Waimanalo, HI (US)

(72) Inventor: David N. Fell, Jr., Waimanalo, HI (US)

(73) Assignee: Fantastic Gardens Hawaii, Inc., Waimanalo, HI (US)

( * ) Notice: Subject to any disclaimer, the term of this patent is extended or adjusted under 35 U.S.C. 154(b) by 200 days.

(21) Appl. No.: 13/998,473

(22) Filed: Nov. 4, 2013

(51) Int. Cl.
*A01H 5/12* (2006.01)

(52) U.S. Cl.
USPC ..... Plt./381

(58) Field of Classification Search
USPC ..... Plt./381
See application file for complete search history.

*Primary Examiner* — Anne Grunberg
(74) *Attorney, Agent, or Firm* — C. A. Whealy

(57) ABSTRACT

A new and distinct cultivar of *Philodendron* plant named 'Little Hope', characterized by its relatively compact, upright and mounding plant habit; freely basal branching habit; dense and bushy plant form; vigorous and robust growth habit; relatively small dark green-colored leaves; and relative resistance to pathogens common to *Philodendron* plants.

1 Drawing Sheet

Botanical designation: *Philodendron selloum.*
Cultivar denomination: 'LITTLE HOPE'.

BACKGROUND OF THE INVENTION

The present invention relates to a new and distinct cultivar of *Philodendron* plant, botanically known as *Philodendron selloum* and hereinafter referred to by the name 'Little Hope'.

The new *Philodendron* plant is a naturally-occurring whole plant mutation of *Philodendron selloum* 'Hope', not patented. The new *Philodendron* plant was discovered and selected by the Inventor in 2009 as a single plant from within a population of plants of 'Hope' in a controlled greenhouse environment in Waimanalo, Hi.

Asexual reproduction of the new *Philodendron* plant by micro-propagated cuttings in a controlled environment in Waimanalo, Hi. since 2010 has shown that the unique features of this new *Philodendron* plant are stable and reproduced true to type in successive generations of asexual reproduction.

SUMMARY OF THE INVENTION

Plants of the new *Philodendron* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Little Hope'. These characteristics in combination distinguish 'Little Hope' as a new and distinct *Philodendron* plant:

1. Relatively compact, upright and mounding plant habit.
2. Freely basal branching habit; dense and bushy plant form.
3. Vigorous and robust growth habit.
4. Relatively small dark green-colored leaves.
5. Relatively resistant to pathogens common to *Philodendron* plants.

Plants of the new *Philodendron* differ from plants of the parent, 'Hope', in the following characteristics:

1. Plants of the new *Philodendron* are more compact and denser than plants of 'Hope'.
2. Plants of the new *Philodendron* are more freely basal branching than plants of 'Hope'.
3. Plants of the new *Philodendron* have smaller leaves than plants of 'Hope'.
4. Plants of the new *Philodendron* have exhibited resistance to Dasheen Mosaic Virus and *Erwinia* whereas plants of 'Hope' are susceptible to Dasheen Mosaic Virus and *Erwinia.*

Plants of the new *Philodendron* can be compared to plants of *Philodendron selloum* 'Winterbourn', disclosed in U.S. Plant Pat. No. 7,030. Plants of the new *Philodendron* differ from plants of 'Winterbourn' in the following characteristics:

1. Plants of the new *Philodendron* are more compact than plants of 'Winterbourn'.
2. Plants of the new *Philodendron* are more freely basal branching and denser than plants of 'Winterbourn'.
3. Leaves of plants of the new *Philodendron* have deeper sinuses than leaves of plants of 'Winterbourn'.

BRIEF DESCRIPTION OF THE PHOTOGRAPHS

The accompanying photographs illustrate the overall appearance of the new *Philodendron* plant showing the colors as true as it is reasonably possible to obtain in colored reproductions of this type. Colors in the photographs may differ slightly from the color values cited in the detailed botanical description which accurately describe the colors of the new *Philodendron* plant.

The photograph at the bottom of the sheet comprises a side perspective view of a typical plant of 'Little Hope' grown in a container.

The photograph at the top of the sheet is a close-up view of a typical plant of 'Little Hope'.

DETAILED BOTANICAL DESCRIPTION

The aforementioned photographs and following observations and measurements describe plants grown during the summer in 25-cm containers in an outdoor nursery in Waimanalo, Hi. and under cultural practices typical of commercial *Philodendron* production. During the production of the plants, day temperatures ranged from 18° C. to 32° C., night temperatures ranged from 13° C. to 25° C. and light levels ranged from 7,000 to 18,000 foot-candles. Plants were nine months old when the photographs and the detailed description were taken. In the following description, color references are made to The Royal Horticultural Society Colour Chart, 2007 Edition, except where general terms of ordinary dictionary significance are used.

Botanical classification: *Philodendron selloum* 'Little Hope'.

Parentage: Naturally-occurring whole plant mutation of *Philodendron selloum* 'Hope', not patented.

Propagation:

*Type*.—By micro-propagated cuttings.

*Time to produce a rooted young plant, summer*.—About 60 days at 27° C. soil and 29° C. air temperatures.

*Time to produce a rooted young plant, winter*.—About 70 days at 21° C. soil and 27° C. air temperatures.

*Root description*.—Fibrous, medium in thickness; white in color.

*Rooting habit*.—Freely branching; medium density.

Plant description:

*Plant and growth habit*.—Relatively compact, upright and mounding plant habit; freely basal branching habit; dense and bushy plant form; vigorous and robust growth habit; developing leaves initially upright, then arching outwardly with development.

*Plant height*.—About 54 cm.

*Plant diameter or spread*.—About 86 cm; with subsequent development, plants achieve a diameter of about 122 cm.

*Stem description*.—Branching habit: Plants of the new *Philodendron* are freely basal branching with about 85 basal shoots developing per plant; shoots completely enclosed by petiole sheath bases. Aspect: Mostly upright to slightly outward. Strength: Strong. Internode length: About 4 mm. Texture: Smooth, glabrous. Color: Close to 157B.

Leaf description:

*Arrangement*.—Alternate to whorled; simple.

*Length*.—About 28 cm.

*Width*.—About 22.5 cm.

*Shape*.—Roughly arrowhead-shaped or deltoid with deep sinuses.

*Apex*.—Acute to acuminate.

*Base*.—Hastate.

*Margin*.—Initially, entire to slightly sinuate and becoming deeply dissected with development.

*Texture, upper surface*.—Smooth, glabrous; luster, glossy.

*Texture, lower surface*.—Smooth, glabrous; luster, shiny.

*Venation pattern*.—Pinnate.

*Color*.—Developing leaves, upper surface: Close to 146B. Developing leaves, lower surface: Close to 146B to 146C. Fully expanded leaves, upper surface: Close to N137B; along the margins, close to 145A; venation, close to 137C. Fully expanded leaves, lower surface: Close to 146A; venation, close to 147C.

*Petioles*.—Aspect: Erect to outwardly leaning. Length: About 39 cm. Diameter: About 1.3 cm. Strength: Strong; flexible. Texture, upper and lower surface: Smooth, glabrous; luster, shiny. Color, upper surface: Close to 144B. Color, lower surface: Close to 144A.

Inflorescence description: Inflorescence initiation and development has not been observed on plants of the new *Philodendron.*

Disease & pest resistance: Plants of the new *Philodendron* have exhibited relative resistance to Dasheen Mosaic Virus and *Erwinia*. Plants of the new *Philodendron* not been observed to be resistant to pests and other pathogens common to *Philodendron* plants.

Temperature tolerance: Plants of the new *Philodendron* have been observed to tolerate temperatures ranging from about 4.4° C. to about 46° C.

It is claimed:

1. A new and distinct *Philodendron* plant named 'Little Hope' as illustrated and described.

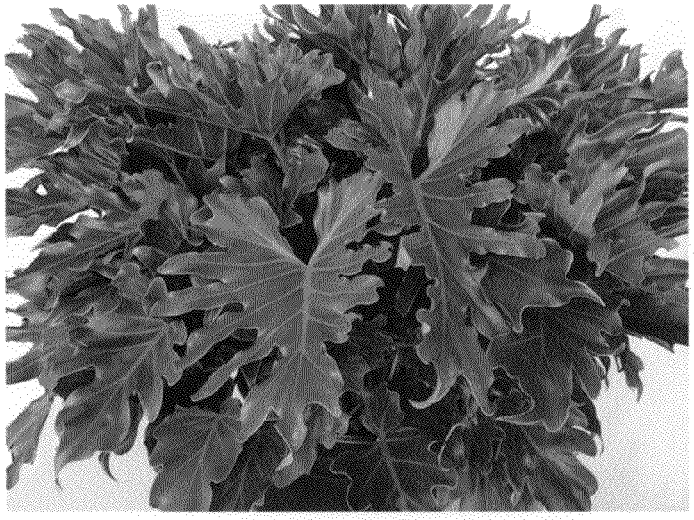
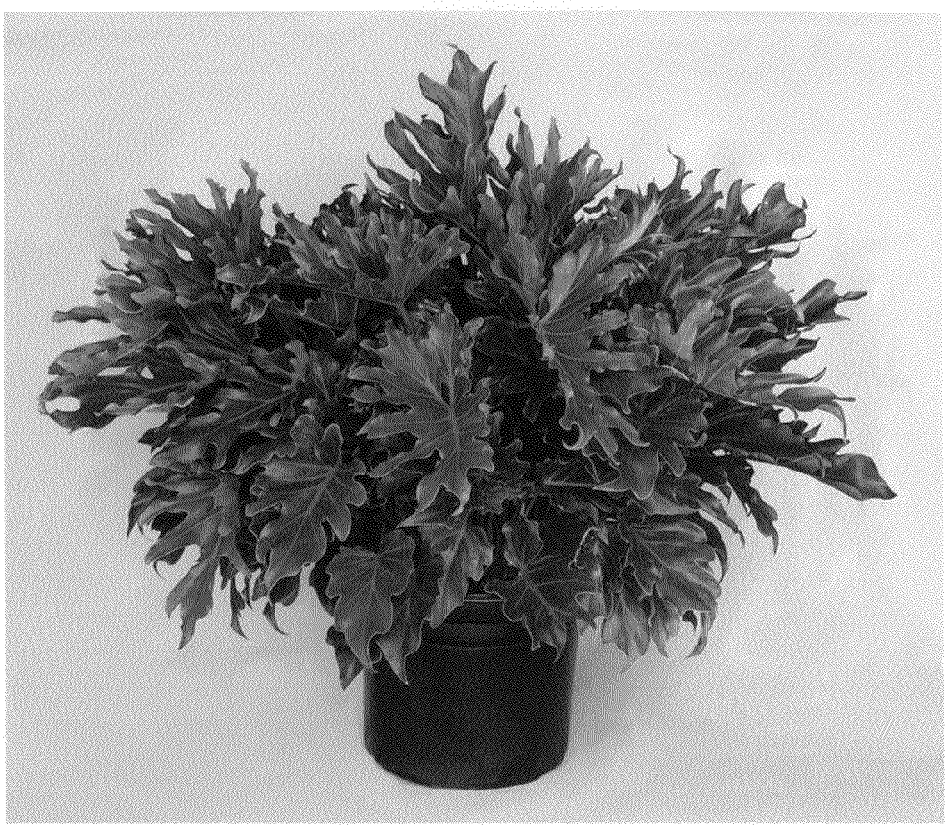

* * * * *